US010548510B2

United States Patent
Brown et al.

(10) Patent No.: US 10,548,510 B2
(45) Date of Patent: Feb. 4, 2020

(54) OBJECTIVE BALANCE ERROR SCORING SYSTEM

(71) Applicants: Harrison James Brown, Vancouver (CA); Jean-Sebastien Blouin, Vancouver (CA); Gunter P. Siegmund, Richmond (CA); Kees Van Den Doel, Vancouver (CA)

(72) Inventors: Harrison James Brown, Vancouver (CA); Jean-Sebastien Blouin, Vancouver (CA); Gunter P. Siegmund, Richmond (CA); Kees Van Den Doel, Vancouver (CA)

( * ) Notice: Subject to any disclaimer, the term of this patent is extended or adjusted under 35 U.S.C. 154(b) by 571 days.

(21) Appl. No.: 14/755,807

(22) Filed: Jun. 30, 2015

(65) Prior Publication Data
US 2017/0000383 A1 Jan. 5, 2017

(51) Int. Cl.
*A61B 5/11* (2006.01)
*A61B 5/00* (2006.01)

(52) U.S. Cl.
CPC ............. *A61B 5/11* (2013.01); *A61B 5/1116* (2013.01); *A61B 5/1122* (2013.01); *A61B 5/4023* (2013.01); *A61B 5/7246* (2013.01)

(58) Field of Classification Search
None
See application file for complete search history.

(56) References Cited

U.S. PATENT DOCUMENTS

| | | | |
|---|---|---|---|
| 7,587,053 B1* | 9/2009 | Pereira | H04R 3/005 381/387 |
| 2002/0060633 A1* | 5/2002 | Crisco, III | A42B 3/046 340/669 |
| 2006/0253001 A1* | 11/2006 | Small | A61B 5/16 600/300 |

(Continued)

FOREIGN PATENT DOCUMENTS

| | | |
|---|---|---|
| WO | 2013038214 A2 | 3/2013 |
| WO | WO 2013038214 A2 | 3/2013 |

(Continued)

OTHER PUBLICATIONS

Howell, D. R., Osternig, L. R., & Chou, L. S. Dual-Task Gait Balance Control Assessment With an Inertial Measurement Unit Following Concussion (Dec. 24, 2014).

(Continued)

*Primary Examiner* — Matthew Kremer
(74) *Attorney, Agent, or Firm* — Benoit & Cote Inc.; Ibrahim Tamer (57) ABSTRACT

A computer implemented system and method for performing a quantitative balance assessment on a subject are described. The method comprises instructing the subject to perform an assessment task with at least a first kinematic sensor mounted on the subject's head; collecting kinematic sensor measurements, comparing the measurements to a threshold value; summing the total number of kinematic sensor measurements that exceed the threshold value to generate a numerical score indicative of the subject's postural stability.

(Continued)

The system makes use of only kinematic data collected from the wireless sensors to quantify BESS, and generate a BESS score, without any other physiological variables such as forward sway.

8 Claims, 10 Drawing Sheets

(56) References Cited

U.S. PATENT DOCUMENTS

| | | | | |
|---|---|---|---|---|
| 2007/0015611 A1* | 1/2007 | Noble | ............... | A61B 5/1116 |
| | | | | 473/450 |
| 2007/0299362 A1* | 12/2007 | Epley | ............... | A61B 5/4863 |
| | | | | 600/559 |
| 2010/0074460 A1* | 3/2010 | Marzetta | ............ | G02C 11/06 |
| | | | | 381/313 |
| 2011/0270117 A1* | 11/2011 | Warwick | ........... | A61B 5/0476 |
| | | | | 600/544 |
| 2011/0270135 A1* | 11/2011 | Dooley | ............ | A61B 5/1121 |
| | | | | 600/595 |
| 2012/0330178 A1* | 12/2012 | Kraft | ............... | A61B 5/6898 |
| | | | | 600/544 |
| 2013/0035613 A1 | 2/2013 | Curtiss | | |
| 2013/0171596 A1 | 7/2013 | French | | |
| 2014/0100486 A1 | 4/2014 | Alberts | | |
| 2014/0347262 A1* | 11/2014 | Paek | ............... | G09G 3/20 |
| | | | | 345/156 |

FOREIGN PATENT DOCUMENTS

| | | | |
|---|---|---|---|
| WO | 2013158095 A1 | 10/2013 | |
| WO | WO 2013158095 A1 | 10/2013 | |
| WO | 2014000045 A1 | 1/2014 | |
| WO | 2014100045 A1 | 6/2014 | |
| WO | WO 2014143896 A2 * | 9/2014 | ......... A61B 5/04842 |
| WO | WO 2014100045 A1 | 6/2016 | |

OTHER PUBLICATIONS

Howell, David R et al. (from 2014 at www.williamette.edu/cla/exsci/nwbs/pdf/Howell.pdf).

* cited by examiner

OBJECTIVE BALANCE ERROR SCORING SYSTEM

BACKGROUND (a) Field

The subject matter disclosed generally relates to quantifying the balance error scoring system or "BESS" to assess concussion severity.

Human standing balance is an established indicator of concussion severity (Guskiewicz K M. 2011. *Clin J. Sports Med.* 30:89-102), and for this reason is incorporated into sports-related concussion evaluation and standard operating protocols in rehabilitation (Cavanaugh, J T Guskiewicz, K M; et al. 2005. *Sports Med.* 35(11):935-50). The problem of limited on-field access to special equipment and the moderate-to-low reliability of simple sideline tests present challenges to managing concussion. Assessment of concussion severity must be made quickly in order to provide the best treatment.

Human standing balance can be assessed by sophisticated means like optical three-dimensional motion tracking systems and force plates which provide precise measurements of the kinematics and kinetics of the human body during standing balance, but these are confined to research laboratories because of space, costs, and set up (Lafond, D; Duarte M. et al. 2004. *J. Biomech.* 37: 1421-6). Automated products such as the Swaymeter™, Berg Balance Scale, and Balance Error Scoring System (BESS) are portable and require minimal training, but have marginal validity, give unreliable scores, and are environment- and tester-dependent (Barlow, M; Shlabach D. et al. 2011. *Int. J Sports Phys Ther.* 6(3):287-95; Bell D R; Guskiewicz K M et al. 2011. *Sports Health.* 3(3):287-95; Onate J A; Beck B C; et al. 2007. *J Athl Train.* 42(4): 445-51; Valovich-Mclead T C; Perrin D H; et al. 2003. *J. Athl. Train.* 38:51-6). Studies have reported poor reliability both between different raters (ICC=0.74) and for one rater grading the same test twice (ICC=0.57 (Finoff J T; Peterson J J; et al. 2009. P M. R. 1(1):50-4)). This suggests that BESS scores must change by almost 50% before the difference can be attributed to changes in balance rather than rater judgment variability (Finoff J T, 2009).

As a result, there is no reliable method to perform accurate balance assessment on the sideline (Clark M A et al. 2011) or in a small medical facility.

(b) Related Prior Art

In Furman G R, Lin C-C, Bellanca J, et al. 2013. *Am J Sports Med.* 20 (10), BESS was found to be better than balance accelerometer measure (BAM). In Howell, David R et al., 3D analysis using a ten camera motion analysis system is disclosed. In King et al. 2014. *Arc Phys Med* 95, the use of an Opal™ inertial sensor fastened at lumbar 5 with an elastic belt is disclosed. The Opal includes 2 linear accelerometers (mediolateral and AP) to detect postural sway.

US patent publication No. 20130035613 discloses a mobile phone application to test balance. In Patterson, Jeremy A. et al. 2014. *Int J Athletic Therapy & Training*, a mobile "app" by SWAY Medical LLC was compared to traditional BESS.

PCT publication WO201400045 discloses use of a sensor mat to determine at least two characteristics of a subject's activity by using a combination of sensors for force and foot orientation/motion/position.

US Patent Publication No. 20130171596 discloses a neurological assessment apparatus with multiple contact points and using visuals to elicit responses.

US Patent Publication No. 20140100486 discloses a computerized method for analyzing balance and vestibule-ocular reflex data. This disclosure describes data processing but says little about data acquisition.

PCT Publication WO2013/038214 discloses a "smart" shoe insole for gait analysis. PCT Publication WO2014/100045 discloses foot sensors which are connected to hardware on or near the foot. PCT Publication WO2013/158095 discloses the use of an accelerometer to assess patient safety.

There remains a need for an objective BESS System ("oBESS") that is portable, inexpensive, and consistent, for assessing the severity of concussion on the field or in emergency medical clinics.

SUMMARY

According to an embodiment of the invention, there is provided a computer implemented method for performing a quantitative balance assessment on a subject, the method including the steps of: (a) having or instructing the subject perform an assessment task with at least a first kinematic sensor mounted on the subject's head; (b) collecting in a computer memory a plurality of kinematic sensor measurements from said at least one first kinematic sensor during at least one time window while the subject is performing said assessment task; (c) comparing in a processor ones of said first plurality of kinematic sensor measurements to a threshold value; (d) summing in said processor the total number of said plurality of kinematic sensor measurements that exceed said threshold value to thereby generate at least a first numerical score indicative of the subject's postural stability.

In another embodiment, the method further includes comparing the first numerical score to a reference score.

In another embodiment, the kinematic sensor measurements include linear acceleration measurements.

In another embodiment, the kinematic sensor measurements are linear acceleration measurements and are collected only from a head mounted kinematic sensor.

In an embodiment, the first numerical score is compared to a reference score.

In yet another embodiment, the numerical score is a BESS score and is calculated using a mathematical equation, preferably a polynomial equation.

In another embodiment, the method includes calculating a product of the number of said at least one time window wherein said threshold value is exceeded.

In another embodiment, the method includes the polynomial equation having the general formula: oBESS=c1 R1+c2R2+c3R3+c4, wherein c=a conversion coefficient; and R=the error rate of the subject. In another embodiment, a plurality of time windows is employed.

In another embodiment, the method includes a) detecting a change in postural stability of the subject; or b) evaluating the likelihood of a sport related injury; or c) evaluating the likelihood of a sport related injury by detecting a change in the postural stability of the subject.

In an embodiment, of the invention, there is provided a computer system for performing an objective assessment of a subject's postural stability, the system including at least one head mountable kinematic sensor, a transmitter, and a processor: a) the transmitter for transmitting data from the at least one head mountable kinematic sensor to the processor; b) the processor for receiving the data from the transmitter and summing the data from at least one time window in which the data exceeds a threshold value to thereby generate a numerical score indicative of the postural stability of the subject.

In an embodiment of the invention, the system includes only one kinematic sensor. In an embodiment of the invention, the generating includes comparing the numerical score to a reference score.

In another embodiment, the kinematic sensor measurements include linear acceleration measurements.

In another embodiment, the system further includes comparing the numerical score to a reference score. In another embodiment, the numerical score is a BESS score and the processor calculates said numerical score using a polynomial equation.

In another embodiment, the system includes a processor which possesses a) a memory, and segments data into at least one time window and stores window specific data in the memory; b) multiplies by a coefficient said number of windows wherein said data exceeds a threshold value, to thereby calculate a numerical score; and c) compares said numerical score to a reference value to thereby detect a change in the subject's postural stability.

A system according to an embodiment of the invention wherein said processor calculates a product of the number of said at least one time window wherein the threshold is exceeded.

In another embodiment, the method includes a polynomial equation having the general formula: $oBESS = c1R1 + c2R2 + c3R3 + c4$ wherein $c = a$ conversion coefficient, and $R =$ the error rate of the subject.

In another embodiment, the computer system includes a visual display of the results of the objective assessment.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

BRIEF DESCRIPTION OF THE DRAWINGS

Further features and advantages of the present disclosure will become apparent from the following detailed description, taken in combination with the appended drawings, in which.

DETAILED DESCRIPTION

In embodiments there are disclosed a computer implemented method for performing a quantitative balance assessment on a subject, namely a person, particularly one who is involved in an activity wherein concussions are a risk. As a baseline and for subsequent diagnostic testing, the subject performs an assessment task like BESS with at least one kinematic sensor mounted on his/her head. Briefly stated, the embodiments make use of only kinematic data collected from the wireless sensors to quantify BESS, and generate a BESS score, without any other physiological variables such as forward sway.

Figure 9:
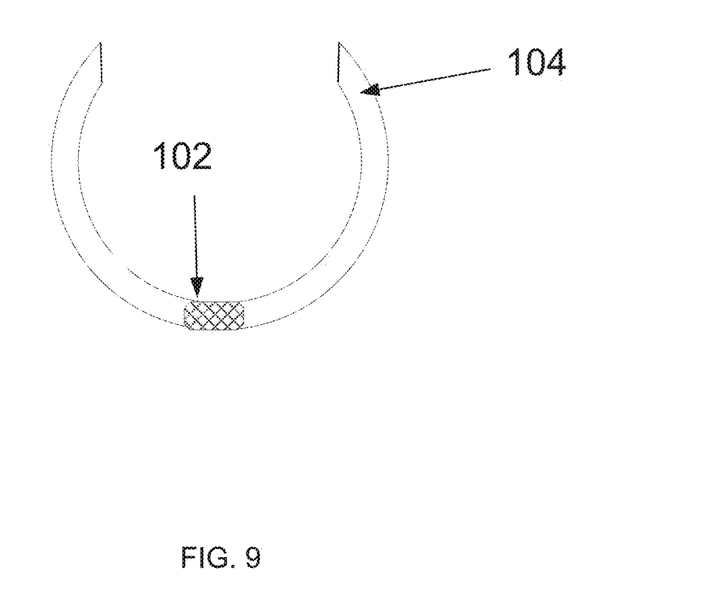
FIG. 9 illustrates an example of a headband having a different shape.

With reference to FIG. 9, there is shown an exemplary system for performing a quantitative balance assessment on a subject, in accordance with an embodiment. As shown in the example of FIG. 9, the system 100 may include a sensor 102 provided in a headband 104 for mounting on the subject's head (not shown). As discussed below, the sensor 102 capture three dimensional linear acceleration data and transmits this data to a computing device 106 for processing. The computing device is preferably a portable computing device such as a smartphone, tablet, and IPOD® device, or any computing device having sufficient hardware and software resources that allows it to implement the present embodiments. The headband 104 may be elastic or rigid, may be made of different materials, and may have different shapes and configurations. The embodiments are not limited to a headband and the sensor 102 may also be embedded in other head worn garments.

The sensor 102 may communicate with the device 106 over a wireless link 108 such as Bluetooth, Wi-Fi or the like. A dedicated app may be provided for installing on the device 106 for receiving and processing the measurement data sent by the sensor 102, as discussed in further detail herein below.

Among other things, the present embodiments may be embodied as methods or devices (portable devices, servers, computer storage media, etc.). Accordingly, the embodiments may take the form of an entirely hardware embodiment, an entirely software embodiment, an embodiment combining software and hardware aspects, a user interface, etc.

"Assessment task" is intended to mean one or some or all of the poses of BESS.

The term "BESS" is intended to mean balance error scoring system, which involves three different balance stances on two different surfaces under the observation of an human tester.

The term "mBESS" is intended to mean modified balance error scoring system including fewer measurements, but similar to BESS.

The term "oBESS" is intended to mean objective balance error scoring system, wherein subjectivity and human error are eliminated.

The sensors are in some embodiments associated with "Inertial measurement units or "IMU". IMU is intended to mean an electronic device that measures and reports velocity, acceleration, orientation, and gravitational forces, for a detailed record of motion, using a combination of accelerometers and gyroscopes, sometimes also magnetometers.

Thus, in embodiments of the invention, Inertial Measurement Units or IMU data are collected via sensors, (one example is Shimmer™ of Realtime Technologies Ltd., Dublin, Ireland) which wirelessly transmit six types of kinematic data (linear accelerations and angular velocities, each in three dimensions) at a particular frequency, in one embodiment 102.4 Hz. The resultant data is transmitted real time to a computer memory. In one embodiment, a custom LabVIEW™ program (National Instruments, Austin, Tex.) is used. In embodiments of the invention, the computer memory is housed in a standard PC, smart phone or tablet. In embodiments of the invention, the computer is housed in a purpose dedicated handheld device.

IMU readers or sensors are secured to the subjects with elastic straps or clips. In embodiments, the sensors may be built into a hat or clothing, or removable from a pocket in these articles. The latter would allow the garment to be washed.

The method includes collecting in a computer memory a plurality of kinematic sensor measurements from said at least one first kinematic sensor during at least one time window while the subject is performing the balance assessment task; comparing signals of the sensor to a threshold value; summing the total number of measurements that exceed the threshold value to generate a numerical score indicative of the subject's postural stability.

In embodiments of the invention, the method further includes comparing said first numerical score to a reference score. The kinematic sensor measurements comprise linear acceleration measurements in some embodiments. Linear acceleration is merely acceleration along a straight line. It remains a component of angular acceleration. The kinematic sensor measurements are linear acceleration measurements and are collected only from said head mounted kinematic sensor.

In embodiments of the invention, the method includes comparing first numerical score to a reference score. In embodiments of the invention, the numerical score is a BESS score and is calculated using a polynomial equation, namely calculating a product of the number of said at least one time window wherein the threshold value is exceeded.

In embodiments of the invention, the polynomial equation has the general formula: $oBESS = c_1 R_1 + c_2 R_2 + c_3 R_3 + c_4$ wherein
c=a conversion coefficient; and
R=the error rate of the subject.

In embodiments of the invention, the method uses a plurality of time windows.

In embodiments of the invention, a method is disclosed for:
a) detecting a change in postural stability of a subject; and
b) evaluating the likelihood of a sport related injury; and
c) evaluating the likelihood of a sport related injury by detecting a change in the postural stability of the subject.

In embodiments of the invention, a computer system for performing an objective assessment of a subject's postural stability includes at least one head mountable kinematic sensor, a transmitter, a receiver and a processor: the transmitter for transmitting data from the at least one head mountable kinematic sensor to the processor; the receiver and processor for receiving the data from the transmitter and summing the data from at least one time window in which the data exceeds a threshold value to thereby generate a numerical score indicative of the postural stability of the subject.

The computer equipment required for oBESS includes sensor or sensors associated physically with the subject being tested, and a computer with a receiver, processor, and memory. Sensor data is kinematic, linear acceleration data. Data is processed, and processed data is observable via a plotting device or a graphical user display or interface.

In embodiments of the invention, a graphical user display is used to list the instructions for BESS stances. In others, it includes a timer which counts down the 20 second intervals. In embodiments of the invention, the display shows a numerical score for each stance and the final total.

The protocol of the invention is, in embodiments of the invention, embedded in the computer memory, and is available to process incoming data and be run on that data to generate a result.

In embodiments of the invention, the system comprises only one kinematic sensor. One sensor is chosen to reduce cost and reduce complexity.

In embodiments of the invention, the system processor includes a memory, and partitions or segments said data into at least one time window and stores said window specific data in said memory; then multiplies the number of windows by a coefficient when the data exceeds the threshold value, to calculate the numerical score; and compares the numerical score to a reference value to detect a change in the subject's postural stability.

In embodiments of the invention, the system processor calculates a product of the number of said at least one time window wherein the threshold is exceeded. The polynomial equation $oBESS = c_1 R_1 + c_2 R_2 + c_3 R_3 + c_4$ (c is conversion coefficient and R is the error rate of the subject) is embedded in the memory of the computer system. In embodiments of the invention, the computer system has a display for displaying the results of said objective assessment.

Referring now to the drawings, all show data for forehead mounted IMU only. More particularly referring to FIG. 1, a graph showing sample raw tri-axial linear acceleration data from oBESS calculation using linear acceleration only, the signals created by a sensor located on a human subject.

Figure 2:
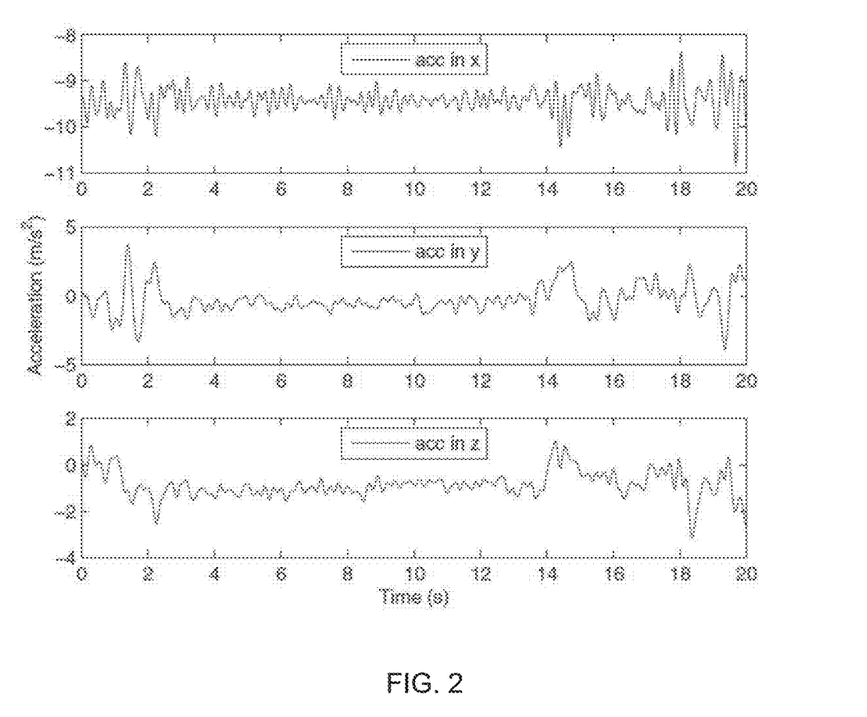
FIG. 2 illustrates filtered tri-axial linear acceleration data from oBESS Calculation Using Linear Acceleration Only, forehead mounted IMU only.

Now referring to FIG. 2, there is shown filtered tri-axial linear acceleration data from oBESS calculation using linear acceleration only.

Figure 3:
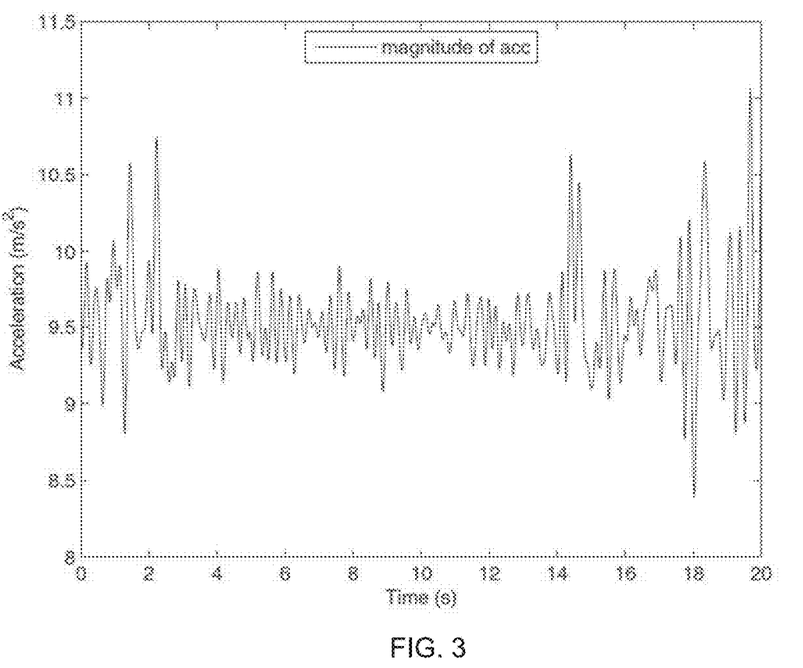
FIG. 3 illustrates magnitude of linear acceleration vector data from oBESS Calculation Using Linear Acceleration Only, forehead mounted IMU only.

Now referring to FIG. 3, there is shown magnitude of linear acceleration vector data from oBESS calculation using linear acceleration only.

Figure 4:
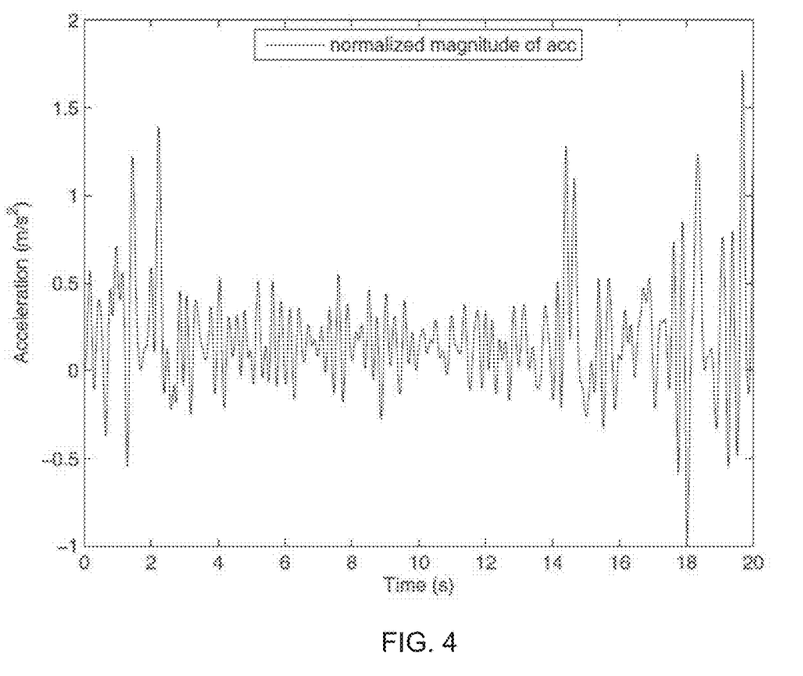
FIG. 4 illustrates normalized linear acceleration vector data from oBESS Calculation Using Linear Acceleration Only, forehead mounted IMU only.
Figure 5:
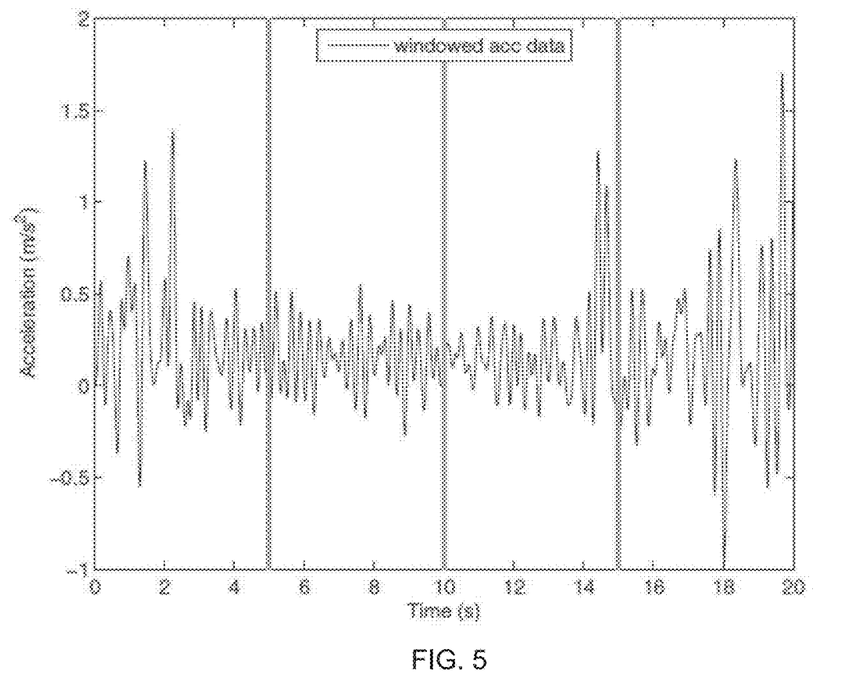
FIG. 5 illustrates linear acceleration vector data from oBESS Calculation Using Linear Acceleration Only, forehead mounted IMU only divided into four five-second windows.

Referring to FIG. 4, there is shown normalized linear acceleration vector data from oBESS calculation using linear acceleration only, forehead mounted IMU only. In FIG. 5 there is shown linear acceleration vector data from oBESS calculation using linear acceleration only, divided into four five-second windows.

Figure 6:
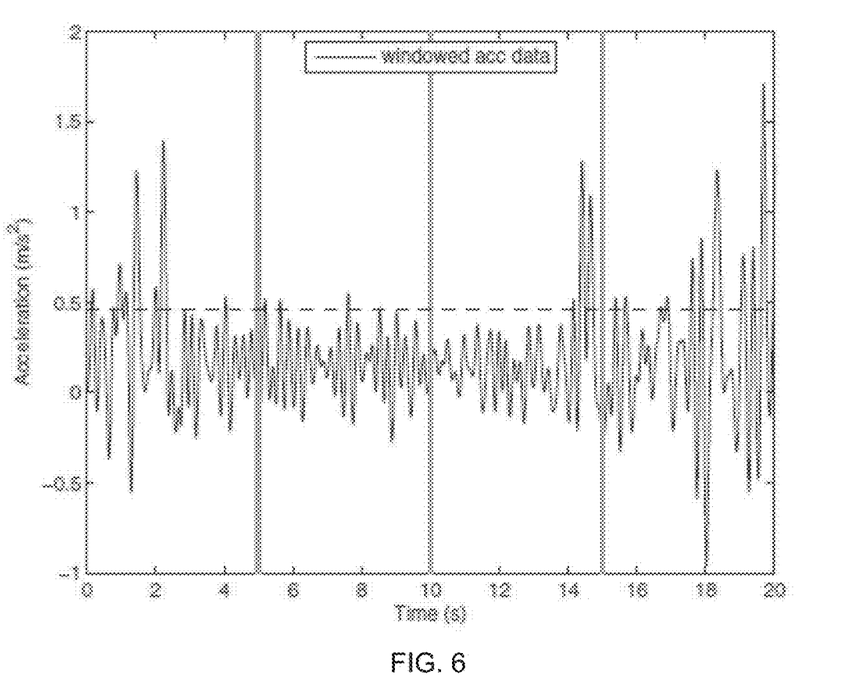
FIG. 6 illustrates linear acceleration data from oBESS Calculation Using Linear Acceleration Only, forehead mounted IMU only split into 4 windows and plotted with a positive balance error threshold of 1.5× standard deviations of the signal.

Finally, in FIG. 6 linear acceleration data from oBESS calculation using linear acceleration only is shown, split into 4 windows and plotted with a positive balance error threshold of 1.5× standard deviations of the signal.

BESS is the current standard for assessing standing balance in concussed athletes on the sideline (Guskiewicz K M, 2011).

The standard Balance Error Scoring System (BESS) developed by researchers and clinicians at the University of North Carolina's Sports Medicine Research Laboratory, Chapel Hill, N.C. The protocol is used in embodiments of the invention, and includes two testing surfaces: floor/ground and foam pad.

For Floor/Ground: Any level surface may be used. For the foam surface, provide one that is at least 10 by 10 inches and 2.5 inches thick. The foam pad creates an unstable surface and a more challenging balance task.

A timer is needed for timing the subjects during the six 20 second trials, a spotter/assistant to assist the subject should he/she start to fall, and the BESS Testing Protocol instructions read or prerecorded for the subject to follow during administration of the BESS. There must be a score card or computer memory to record balance errors made. In embodiments of the invention, a computer memory is used to collect and retain the balance error data.

Before testing, the subject removes his or her shoes and any ankle taping. The instructions below are read or played back to the subject and errors are recorded.

Scoring the BESS

Each 20 second trial is scored by counting the errors, or deviations from the stance, accumulated by the subject. The observer will begin counting errors only after the individual has assumed the proper testing position. Errors include: moving the hands off of the iliac crests, opening the eyes, step stumble or fall abduction or flexion of the hip beyond 30°, lifting the forefoot or heel off of the testing surface, or remaining out of the proper testing position for greater than 5 seconds.

The maximum total number of errors for any single condition is 10.

TABLE 1

Normal Scores for Each Possible Testing Surface
(University of North Carolina's Sports Medicine
Research Laboratory, Chapel Hill, NC).

|  | Firm Surface (out of 10) | Foam Surface (out of 10) |
| --- | --- | --- |
| Double Leg Stance | .009 ± .12 | .33 ± .90 |
| Single Leg Stance | 2.45 ± 2.33 | 5.06 ± 2.80 |
| Tandem Stance | .91 ± 1.36 | 3.26 ± 2.62 |
| Surface Total | 3.37 ± 3.10 | 8.65 ± 5.13 |

The BESS Total Average Score is 12.03 ± 7.34. The maximum possible score is 30.

If a subject commits multiple errors simultaneously, only one error is recorded. Subjects that are unable to maintain the testing procedure for a minimum of five seconds are assigned the highest possible score, ten, for that testing condition.

The Stances

Double leg stance: standing with feet side by side (touching), hands on the hips and eyes closed.

Single leg stance: standing on a firm surface on the non-dominant foot, the hip is flexed to approximately 30° and knee flexed to approximately 45°. Hands are on the hips and eyes are closed. The non-dominant leg is defined as the opposite leg of the preferred kicking leg Tandem stance: standing heel to toe with the non-dominate foot (defined above) in the back. Heel of the dominant foot should be touching the toe of the non-dominant foot. Hands are on the hips and their eyes are closed.

Sample text for the BESS Testing Protocol Direction to the subject:

This test will consist of 6-twenty second tests with three different stances on two different surfaces. You will hear the stances described as we go.

DOUBLE LEG STANCE: Direction to the subject: The first stance is standing with your feet together with your hands on your hips with your eyes closed. Try to maintain stability for the full 20 seconds. I will record the number of times you move out of this position. If you do move out of the testing stance, simply open your eyes, regain your balance, get back into the testing position as quickly as possible, and close your eyes again. Direction to the spotter: You are to assist the subject if they fall during the test and to help them get back into the position. Direction to the subject: Put your feet together, put your hands on your hips and when you close your eyes the testing time will begin [Start timer when subject closes their eyes]

SINGLE LEG STANCE: Direction to subject: If you were to kick a ball, which foot would you use? Stand on the other (non-dominant) foot. [The dominant leg should be held in approximately 30 degrees of hip flexion and 45 degrees of knee flexion]. Please try to maintain stability for 20 seconds with your eyes closed and your hands on your hips. When you close your eyes the testing time will begin. [Start timer when subject closes their eyes] Direction to the spotter: The spotter should assist the subject if they fall during the test and to help him get back into the position.

TANDEM STANCE: Directions to the subject: Now stand heel-to-toe with your non-dominant foot in back. Your weight should be evenly distributed across both feet. Try to maintain stability for 20 seconds with your eyes closed and your hands on your hips. When you close your eyes the testing time will begin. [Start timer when subject closes their eyes]. The spotter will assist the subject if they fall during the test and to help them get back into the position.

Repeat each set of instructions for the foam pad surface.

Score Card Balance Error Scoring System (BESS) (Guskiewicz) Types of Errors: 1. Hands lifted off iliac crest 2. Opening eyes 3. Step, stumble, or fall 4. Moving hip into >30 degrees abduction 5. Lifting forefoot or heel 6. Remaining out of test position >5 sec The BESS is calculated by adding one error point for each error during the 6 20-second tests.

There are other balance assessment tools and technologies in which the oBESS embodiments find use.

These include: Swaymeter, Berg Balance Scale (BBS), and Romberg's Test.

The method of the invention could be modified to be applied to some "dynamic" balance tests that involve movement like walking or jumping, in one embodiment, by looking at certain time-points in the dynamic motion (e.g. when feet are on the ground).

Such dynamic tests include: Star Excursion Balance Test (SEBT);

Balance Evaluations Systems Test (BEST);

Modified BASS Test.

It will be apparent that in contrast to older methods, the invention makes use of only kinematic data collected from the wireless sensors to quantify BESS, and generate a BESS score, not other physiological variables such as forward sway.

Figure 7A:
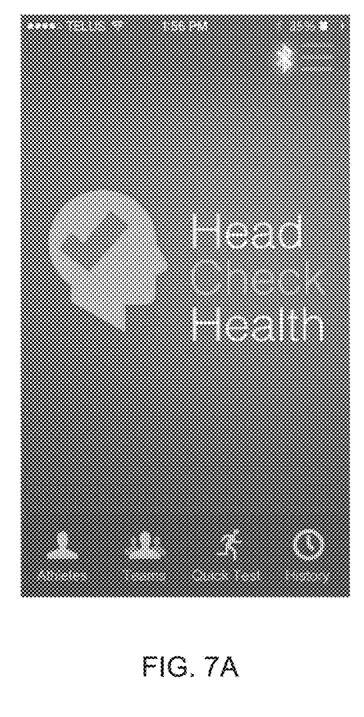
FIGS. 7a to 7o are screen shots illustrating the user interface at different testing stages, in a non-limiting example of the embodiments.
Figure 7B:
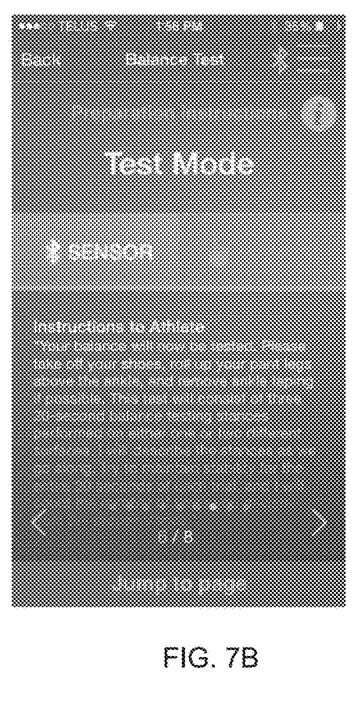
Figure 7C:
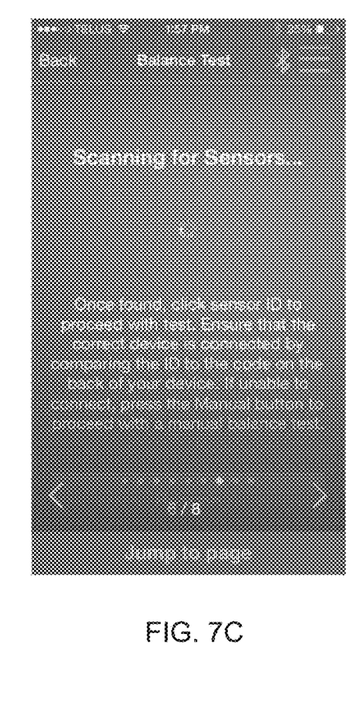
Figure 7D:
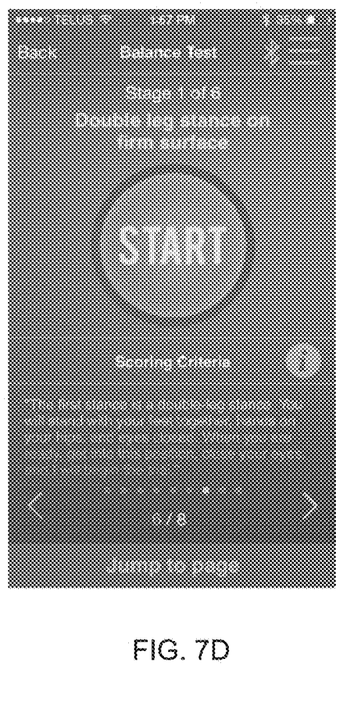
Figure 7E:
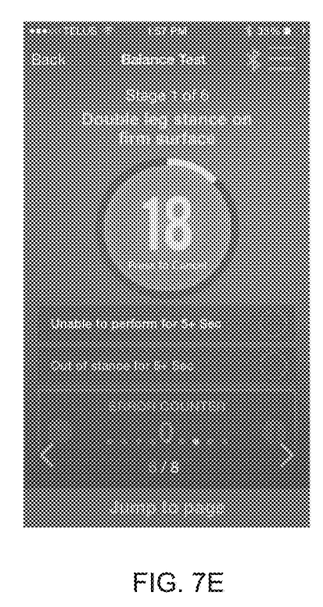
Figure 7F:
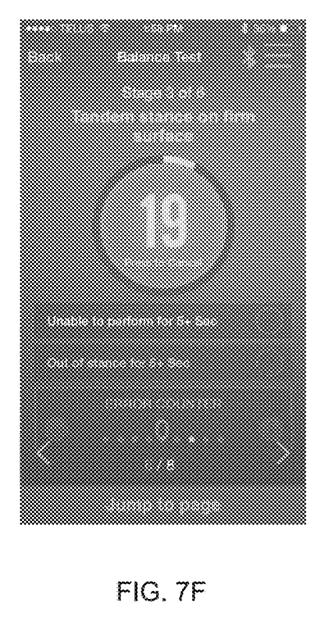
Figure 7G:
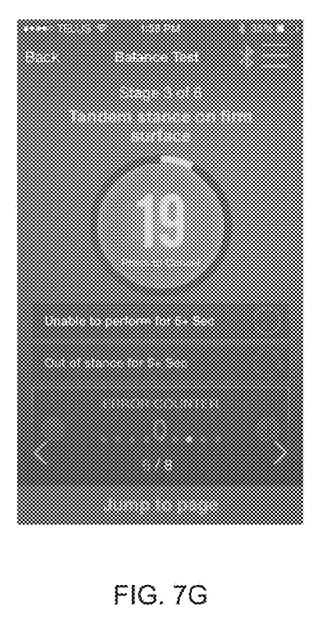
Figure 7H:
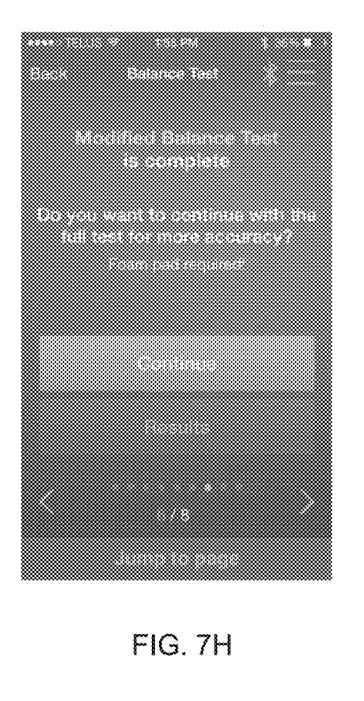
Figure 7I:
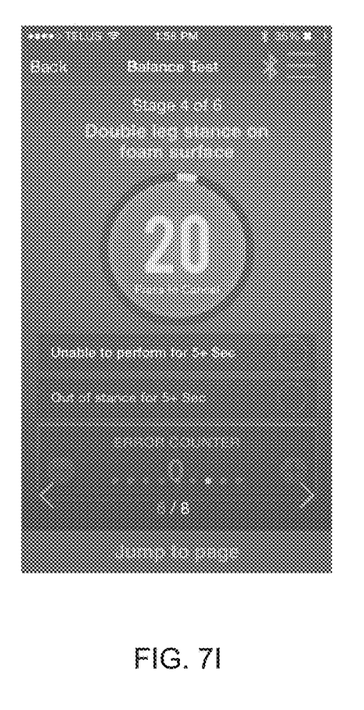
Figure 7J:
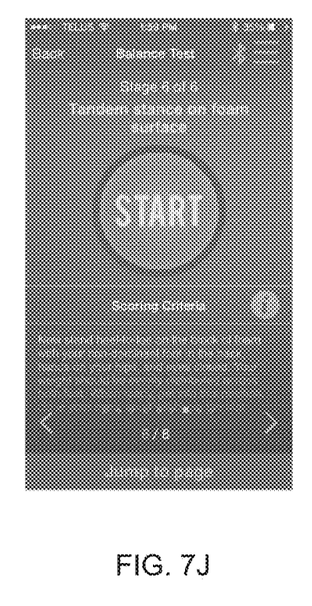
Figure 7K:
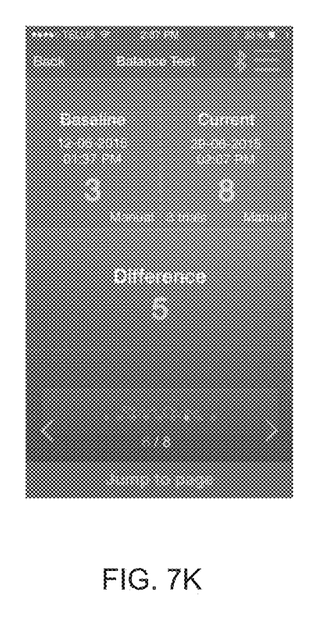
Figure 7L:
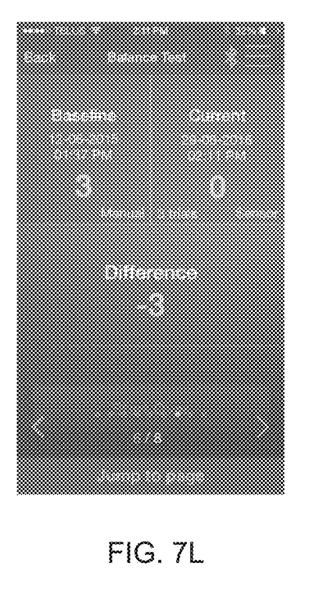
Figure 7M:
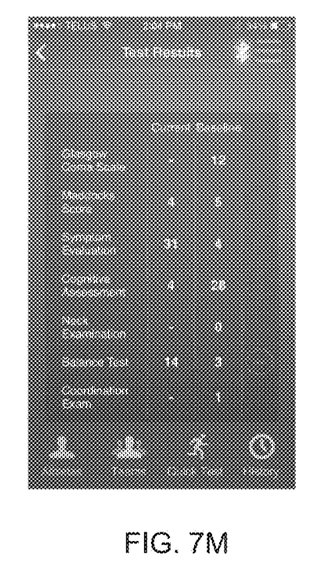
Figure 7N:
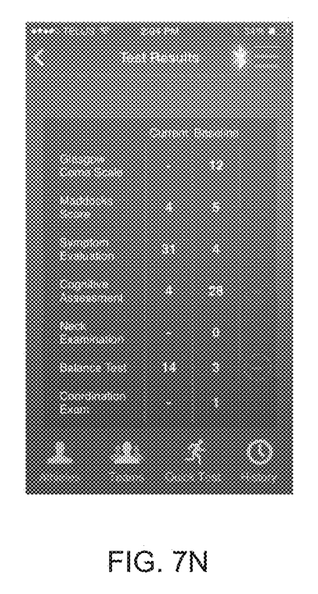
Figure 7O:
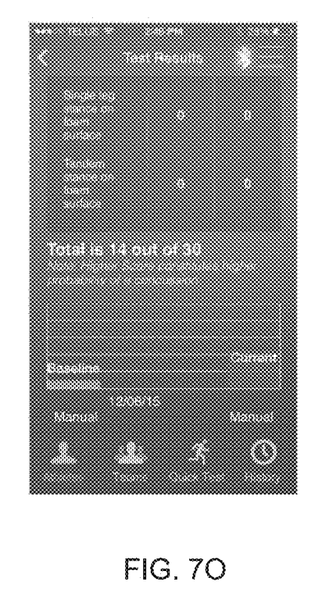
Figure 8:
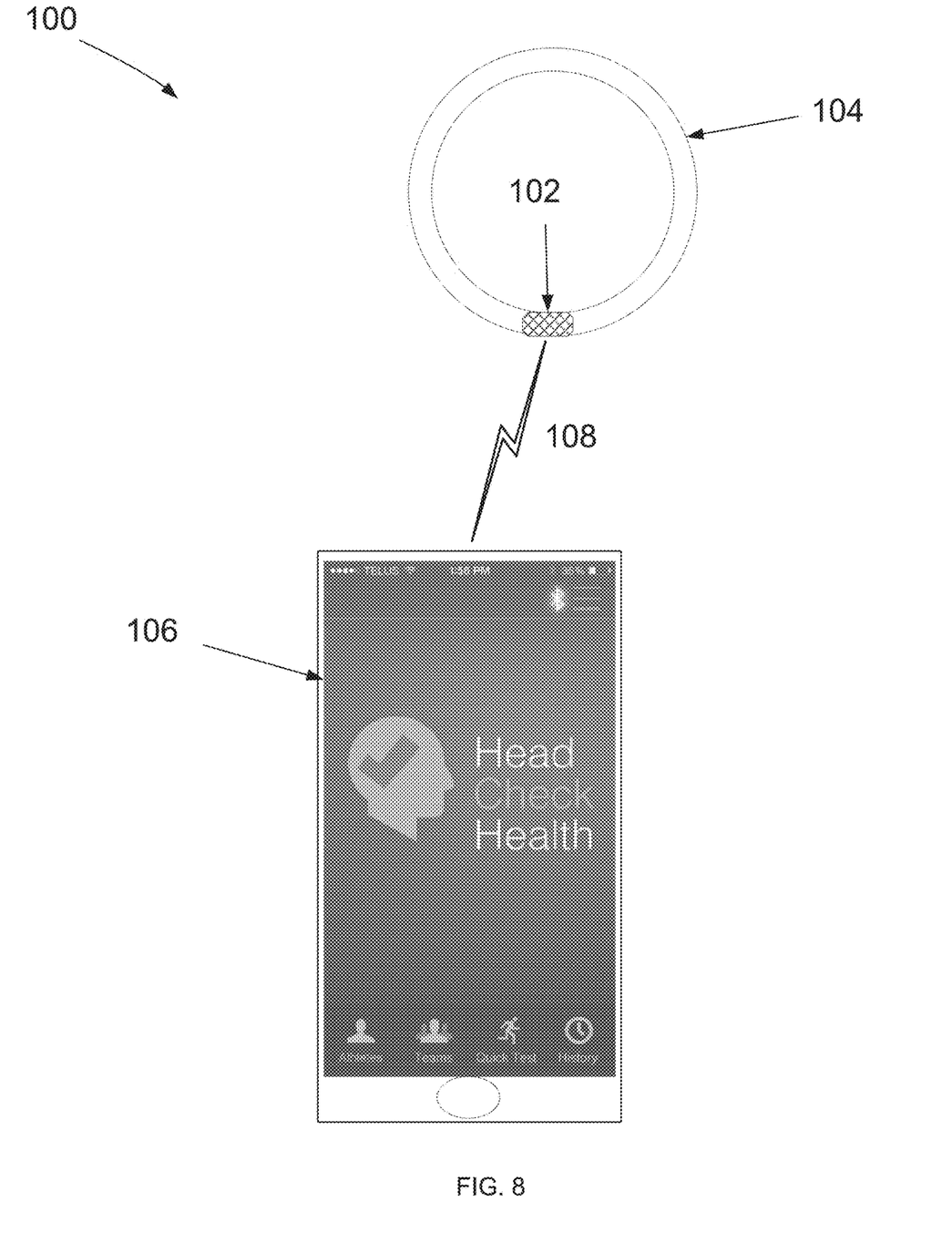
FIG. 8 illustrates an exemplary system for performing a quantitative balance assessment on a subject, in accordance with an embodiment.

FIGS. 7a to 7o are screen shots illustrating the user interface at different testing stages, in a non-limiting example of the embodiments.

FIG. 7a represents the Home Screen. This screen is presented after the user logs into their account. From this screen the user can manage and review their athletes, teams, run a quick test, or review their device's most recent test history. The test function may include 9 batteries: initial assessment, glascow coma scale, maddocks score, symptom evaluation, cognitive assessment, memory test, neck exam, balance test, coordination exam, and delayed memory tests.

FIG. 7b may be presented when the user begins the balance test. This screen includes the preparation instructions, the option of conducting the test manually or via the HeadCheck sensor, and the instructions which are to be read to the athlete at the start of the balance test.

FIG. 7c may be presented when the user selects the sensor test. In which case, the mobile application will scan for bluetooth connections in the area. All sensors available will appear on the list once the app has completed scanning. However only the valid HeadCheck sensors can be connected.

Upon connection, the first of three or six balance stages will appear. Each stage has a similar screen which outlines where the user is within the test, the scoring criteria, the instructions to be read to the athlete before the stage, and has an incorporated timer. FIG. 7 shows stage 1 of the balance test which involves the athlete standing in a double leg stance on a firm surface.

Once the start button has been hit, the timer will begin counting down from 20 seconds as illustrated in FIG. 7e. Users are able to cancel the stage in the event of an error or interruption. When the test is run manually, the user will use the scoring instructions provided and will add (+) errors that they see, including when the athlete is out of stance for 5+ seconds, or when the athlete is unable to perform the test. When the test is run with the HeadCheck sensor, the bottom grading functions are disabled. In an embodiment, the non-manual test score is computed via sensor data+algorithm, so that when the test is run with the HeadCheck sensor, the bottom grading functions are disabled and the score is computed through the sensor data and algorithm.

FIG. 7f illustrates Stage 2 of the balance test which involves the athlete standing in a single leg stance on a firm surface.

FIG. 7g illustrates Stage 3 of the balance test which involves the athlete standing in a tandem stance on a firm surface.

The Balance test can be completed as a modified 3-stage test or it can be completed as a full 6-stage test. FIG. 7h illustrates the screen that allows the user to continue to test the athlete for the full test, or continue with the results from the modified test.

FIG. 7i illustrates Stage 5 of the balance test which involves the athlete standing in a single leg stance on a foam pad/surface.

FIG. 7j illustrates Stage 6 of the balance test which involves the athlete standing in a tandem stance on a foam pad/surface.

When the user completes the modified or full test, they will see a results screen. The results screen may compare scores from the current test to a baseline test that was previously completed as exemplified in FIGS. 7k and 7L. The results screen may also indicate the date and time each test was completed and the difference in score. It may also indicate whether each test was completed manually or by using the HeadCheck sensor, and whether the modified (3 trials) or full (6 trials) was completed.

Upon completion of the full test, the user may be able to see the complete test results, once again comparing the current test scores by test type to the baseline test scores as exemplified in FIGS. 7m, 7n and 7o. In the right hand column, a (+) symbol indicates the score as improved, a (−) symbol indicates the score has declined, and a (=) symbol indicates that the score has remained the same.

In the examples of FIGS. 7n and 7o, when a user clicks on the (+), (−), or (=) sign on the test results screen, they will be able to drill down into the detailed results for that particular test. In this instance, we examine the balance test detailed results. The results show the errors by stage and at the bottom of the screen, shows the total errors for the modified (score out of 30) or the full (score out of 60) test. A visual representation of the graphs is also shown so that test scores over time can be compared.

The present invention will be more readily understood by referring to the following examples which are given to illustrate the invention rather than to limit its scope.

Example 1

Baseline Comparison of Single v. Multiple Sensor Data for BESS

Inertial Measurement Units or IMU data were collected via Shimmer™ sensors, (Realtime Technologies Ltd., Dublin, Ireland) which wirelessly transmitted six types of kinematic data (linear accelerations and angular velocities, each in three dimensions) at 102.4 Hz, and transmitted that data real time to a desktop computer using a custom LabVIEW™ program (National Instruments, Austin, Tex.). IMU readers were secured to the subjects with elastic straps.

Subjects were filmed from the front performing the six standard BESS conditions, i.e., three stances (feet together, one foot, and tandem) on two surfaces (firm surface and medium density foam (SunMate foam; Columbia Foam Inc., BC, Canada). Subjects placed hands on hips and closed their eyes for all tests. Each condition or pose was 20 s long, and were separated by 30 s rests. Video clips were scored by four experienced raters by counting the number of predefined balance errors subjects made during each condition. The standardized balance errors were: moving the hands off hips; opening the eyes; stepping, stumbling, or falling; abduction or flexion of the hip beyond 30 degrees; lifting the ball of the foot or heel off the testing surface; and remaining out of the proper testing position for greater than 5 s.

The maximum number of errors per condition was limited to ten, and the total BESS score was the sum of errors committed during all six conditions. If a subject did not maintain the proper stance for at least 5 s, or did not otherwise complete the condition, he was given the maximum score of ten. An auditory tone (750 Hz, 100-ms duration) was played at the start and end of each 20-s condition. This tone was later used to synchronize the IMU data to the video recordings of the balance tests.

Thirty healthy subjects were filmed performing the Balance Error Scoring System (BESS) while wearing inertial measurement units (IMU) measuring linear accelerations and angular velocities from seven locations of the body: namely forehead, sternum, waist, right and left wrist, and right and left shin.

Each video was then scored by four experienced BESS raters (having 15, 20, 25 and 150 hours of grading experience respectively). Their mean scores were compared to an algorithm computing objective BESS (oBESS) scores solely from IMU data.

Inter-rater reliability and accuracy of BESS scores were assessed using intraclass correlations (ICC). The experienced raters displayed low variability in scoring (ICC3, 1=0.91).

Example 2

Objective Balance Error Scoring (oBESS) Development

An algorithm for use in a computer was developed to score balance error from mechanical IMU data. The algorithm was designed to sum a total number of balance errors committed by the subject over the duration of the conditions being analyzed. The values were used to establish a baseline and to create recorded scores over time or after injury.

The IMU data of Example 1 were sectioned into "windows" of time, and the number of windows in which the data exceeded a threshold value was added to generate a BESS score. Various window lengths, threshold values, number of IMU, and different combinations of data (linear acceleration+angular velocity, a+ω; linear acceleration only, a; and angular velocity data only, and angular velocity data only, U) were tested to determine the highest Interclass correlation (ICC) values.

All IMU data were first low-pass filtered (5 Hz, fourth order Butterworth). For each condition, in a 20 s data segment, two resultants were calculated from the triaxial signals (ax, ay, az, ωx, ωy, ωz) to yield the magnitude of the linear acceleration and angular velocity vectors (|a|, |ω|) for each IMU in each condition. This simplification resulted in a shorter algorithm. "Bias" was controlled for by removing the mean, and then splitting the time dimension into non-overlapping windows varying from one window of 20 s to 40 windows of 0.5 s each. Non-overlapping windows were used to avoid capturing the same error more than once. Eight thresholds of from 0.25 Standard Deviations (SD) to 2.0 SD in increments of 0.25 SD were considered to establish the effect of different magnitudes of balance errors.

Excessively low thresholds can cause false positives, whereas thresholds that are too high may result in false negatives.

Example 3

To determine the most ideal measurement location for a single IMU, and to assess whether a single IMU was effective to quantify BESS.

As discussed in the first example, IMU measurement sensor placements tested included seven locations. We then eliminated one or more locations to test the minimum required to create a reliable oBESS, having IMUs placed, for example at: forehead, sternum, waist, R & L wrist, R & L shin; forehead, chest, waist, R and L wrist; forehead, chest, waist; and forehead only.

A raw error score, R, was then defined as the number of windows in which the established "threshold" was exceeded by any IMU included in the analysis during the conditions being analyzed (firm surface only, foam surface only, both surfaces). A window's error score was binary (1 or 0) and was counted only once even if multiple IMU exceeded their thresholds within the window. When subjects could not maintain the testing stance for a minimum of 5 s, or otherwise could not complete the condition (an automatic 10 in the standard BESS scoring system), a value of 5 was added to the resultant R score for that given condition, because preliminary analyses indicated that adding a value of 10 was not needed since part of the balancing behavior was already incorporated into the data. The Objective BESS or oBESS score for a series of conditions was then calculated using the raw error score R and the following equation:

$$oBESS = c_1 R^3 + c_2 R^2 + c_3 R^3 + c_4 \quad \text{[Equation 1]}$$

The coefficients (c1, c2, c3, c4) were calculated using a least squares fit between the mean of the four raters' BESS scores and the raw error scores R for all included IMU and conditions.

The entire analysis was repeated for each combination of conditions (both surfaces, firm surface only, and foam surface only, all three stances). The predictive ability of the optimal algorithm using IMU data from all six conditions was then assessed by generating coefficients for Equation 1 using data from 29 subjects (subject 30 had balanced on the wrong foot during one condition), and then using these coefficients to predict the missing subject's oBESS score. This "one-by-one" method was repeated as a comparison for each subject, and the resultant oBESS scores were compared with mean rater BESS scores using ICC. For all ICC analyses, comparisons were considered good if the ICC values were greater than 0.75 and moderate to poor if less than 0.75. All analyses were conducted using MATLAB (Version R2012a; TheMathWorks Inc., Natick, Mass.), and where needed, statistical significance was set to P=0.05.

The four human raters showed little variance in their total BESS scores across all subjects ($ICC_{3,1}=0.91$); however, they were less consistent when grading conditions were performed on the firm surface ($ICC_{3,1}=0.82$; mBESS) than the foam surface (ICC3,1=0.95). Subjects committed an average of 9.8±7.1 balance errors: 3.2±3.6 on the firm surface and 6.6±4.1 on the foam surface. Using all six BESS conditions, many different combinations of parameters produced oBESS scores with a good fit to the mean rater scores ($ICC_{3,1}>0.75$). The graded pattern of ICC values within each panel in FIG. 2 showed that the algorithms were relatively insensitive to small changes in the number of windows and the threshold values used. The similarity in the pattern of ICC values between the different panels of FIG. 2 showed that the algorithms were similarly insensitive to the groups of data and number of IMU used. The algorithm with the best fit to the mean rater scores ($ICC_{3,1}=0.94$) had 11 windows (1.8 s long) and a 0.50SD error threshold and used both linear acceleration and angular velocity data from five IMU (forehead, chest, waist, and left and right wrist). Using only one IMU at the forehead, the algorithm that best fit the mean rater scores ($ICC_{3,1}=0.92$) had four windows (5 s long), a 1.50SD error threshold, and relied on linear acceleration data only (Table 1A). This latter simpler algorithm was able to accurately predict individual BESS scores using the "one-by-one" validation method (ICC3,1=0.90, Table 1 B).

Optimal algorithms were determined. One, (ICC3, 1=0.94) had 11 windows (1.8 s long) and a 0.50SD error threshold used both linear acceleration and angular velocity data from five IMU (forehead, chest, waist, and left and right wrist). Using only one IMU at the forehead, the algorithm that best fit the mean rater scores (ICC3,1=0.92) had four windows (5 s long), a 1.50SD error threshold, and relied on linear acceleration data only (Table 1A). This latter simpler algorithm was able to accurately predict individual BESS scores using the "one-by-one" validation method (ICC3, 1=0.90, Table 1B). The best oBESS algorithm for the subset of foam-only conditions accurately fits the mean experienced raters (ICC3,1=0.89), whereas the best oBESS algorithm for the subset of firm-only conditions did not (ICC3, 1=0.68).

TABLE 1

ICC values for the fit of oBESS scores generated using data from a single forehead-mounted IMU and all six balance conditions to the mean rater BESS scores (A), and ICC values for the comparison between the one-by-one predictions and the mean rater BESS score using the same single-IMU algorithm (B).

| | | No. of Windows | | | | |
|---|---|---|---|---|---|---|
| | 1 | 2 | 3 | 4 | 5 | 6 |
| A Threshold (xSD) | 1 | 0.8844 | 0.8890 | 0.9048 | 0.9162 | 0.8891 |
| | 1.25 | 0.8861 | 0.8869 | 0.9065 | 0.8698 | 0.8225 |
| | 1.5 | 0.8897 | 0.8688 | 0.9243 | 0.8060 | 0.7371 |
| | 1.75 | 0.8402 | 0.8199 | 0.8697 | 0.8463 | 0.7652 |
| | 2 | 0.8041 | 0.8709 | 0.8061 | 0.7323 | 0.7909 |
| B Threshold (xSD) | 1 | 0.8269 | 0.8172 | 0.8391 | 0.8846 | 0.8535 |
| | 1.25 | 0.8301 | 0.8323 | 0.8667 | 0.8269 | 0.7675 |
| | 1.5 | 0.8268 | 0.7643 | 0.8973 | 0.7512 | 0.6575 |
| | 1.75 | 0.7357 | 0.6575 | 0.8192 | 0.7585 | 0.6767 |
| | 2 | 0.6765 | 0.8066 | 0.7136 | 0.6028 | 0.6957 |

The "best" algorithm (in bold) and surrounding adjacent window numbers and error thresholds are shown.

The automated oBESS was able to produce scores with accurate fit to these expert raters ($ICC_{3,1}=0.92$) and surprisingly were able to predict individual BESS scores ($ICC_{3,1}=0.90$) using data from just one IMU placed on the forehead.

Example 4 oBESS Calculation Using Linear Acceleration Only

Tested subject has wireless sensor(s) placed on head (forehead), with ±2 g range tri-axial (x, y, z) linear accelerometers and 102.4 Hz sampling rate. Example sensors are a modified Shimmer 3™, or ConnectBlue OLP425.

Sensors collected tri-axial linear acceleration data (acceleration values in x, y, and z axes) with sampling rate above 50 Hz. The single sensor was temporarily affixed to the head of the subject.

Recorded or spoken instructions on balance test footing (Balance Error Scoring System (BESS)) were provided. The tested subject performed BESS condition 1 to 3 or 1 to 6 while linear acceleration data was collected from sensor(s) placed on body. Data was collected by sensor and sent to a recording device (a computer.

After three conditions, the balance test is concluded and a balance score is calculated. This three-condition balance test is termed the "mBESS" and is commonly used in concussion assessment protocols (e.g. Sport Concussion Assessment Tool 3—"SCAT3"). To complete the "full" BESS balance test (which provides more accurate results) the tested individual must complete all six test conditions. The last three test conditions involve the same order/stances as the first three with the only difference being that the tested individual will perform them while standing on a block of foam (aimed decrease postural stability.

For all BESS conditions, length of trial and data collected is 20-seconds. This time may be indicated using a start/stop tone played via the peripheral computing device (e.g. iPhone app).

Figure 1:
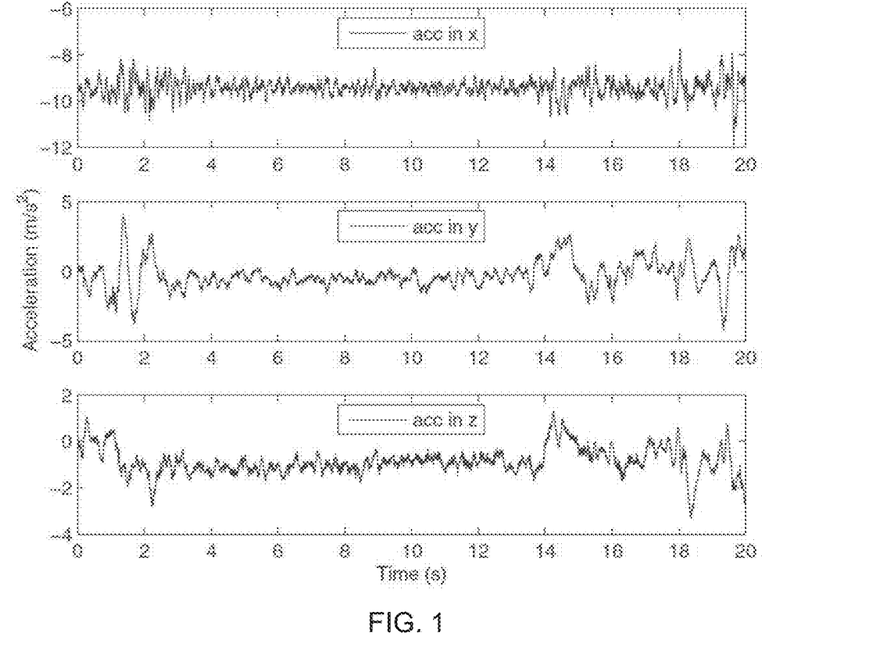
FIG. 1 illustrates Sample raw tri-axial linear acceleration data from oBESS Calculation Using Linear Acceleration Only, forehead mounted IMU only.

Raw Data for the measurement is shown in FIG. 1.

Data Treatment

The 20-s segment of linear acceleration data from all trials (either 3 for mBESS, or 6 from BESS) is low-pass filtered. An example of filter used: 5 Hz (low-pass), $4^{th}$ order Butterworth. FIG. 2 shows the difference this step makes.

To reduce the dimensionality of the data ($a_x$, $a_y$, $a_z \rightarrow |a|$) the magnitude of the linear acceleration vector (lad) is calculated for each sensor used for each condition performed using the following formula:

$$|a|=\sqrt{(a_x^2+a_y^2+a_z^2)}$$

The results are shown in FIG. 3.

Linear acceleration vector(s) are normalized by removing the mean value of the signal from all values. This is done for each sensor for each condition performed. See FIG. 4.

Linear acceleration vector(s) are split into windows. This is done for each sensor for each condition performed. See FIG. 5.

Windows can be overlapping or non-overlapping. Windows can be any value up to 20 s (e.g. 4×5 s windows).

Balance error threshold(s) were calculated for each sensor for each condition performed, using ratios of the standard deviation of the signal (e.g. 1.5×SD). Thresholds can be positive, negative, or both. See FIG. 6 for these effects.

Example 5 oBESS Using Linear Acceleration and Angular Velocity

The data collection was performed as above using Shimmer™ tri-axial gyroscope (or 3 mono-axial gyroscopes). For data analysis methods, the process is very similar as for Example 3, but were carried out for double the amount of signals, both processed using the same methodology. To reduce dimensionality of the data, both the magnitude of the linear acceleration vector(s) ($a_x$, $a_y$, $a_z \rightarrow |a|$) and magnitude of the angular velocity ($w_y$, $w_y$, $w_z \rightarrow |w|$) vector(s) were calculated as for a above. Normalization and threshold calculation were carried out separately for the two types of data (|a| and |w|). Summing of the number of windows exceeded, thereby calculating a raw error score (R), was performed either by summing windows exceeded by either signal (|a| or |w|), or summing windows exceeded by both signals (|a| and |w|).

Example 6 oBESS Using Angular Velocity Only

Data collection and analysis was performed as above, but all computations were done using angular velocity data (w) rather than linear acceleration data (a).

While preferred embodiments have been described above and illustrated in the accompanying drawings, it will be evident to those skilled in the art that modifications may be made without departing from this disclosure. Such modifications are considered as possible variants comprised in the scope of the disclosure.

The embodiments of the invention in which an exclusive right or privilege is claimed are defined as follows:

1. A computer implemented method for performing an objective Balance Error Scoring System (oBESS) on a subject, the method comprising:
   providing a three dimensional (3D) kinematic sensor on a head of the subject;

having the subject perform a balance assessment task for a time period T while having the kinematic sensor on the head performing measurements of 3D kinematic data;

collecting the 3D kinematic data from the kinematic sensor during the balance assessment task;

processing the 3D kinematic data to obtain a linear acceleration vector $|a|=\sqrt{(a_x^2+a_y^2+a_z^2)}$ wherein $a_x$, $a_y$ and $a_z$ represent signal magnitudes along an X axis, a Y axis and a Z axis respectively;

splitting the linear acceleration vector into windows, each window having a candidate duration Tn from a plurality of candidate durations;

comparing a magnitude of the linear acceleration vector in each window to a candidate threshold Thr from a plurality of candidate thresholds;

summing a number of windows having the candidate duration in which the magnitude of the linear acceleration vector exceeded the candidate threshold Thr, to thereby obtain a candidate raw error score (R), repeating the splitting, comparing, and summing steps with a plurality of combinations of other candidate thresholds from the plurality of candidate thresholds and other candidate durations from the plurality of candidate durations such that a plurality of candidate raw error scores are generated;

determining a plurality of candidate polynomial equations for oBESS in which each candidate polynomial equation is determined using a respective candidate raw error score (R) elevated to power n1-nz, with respective candidate polynomial coefficients c1-cz, respectively: $oBESS = c1\,R^{n1} + c2R^{n2} + \ldots + czR^{nz}$;

wherein each candidate polynomial equation is determined by determining the respective candidate polynomial coefficients c1-cz for each respective candidate R using a polynomial fit with a mean of Balance Error Scoring System (BESS) from a plurality of other subjects, and selecting a candidate polynomial equation for oBESS from the plurality of candidate polynomial equations as the polynomial equation of the oBESS on the subject such that the selected candidate polynomial equation maximizes intraclass correlation with the BESS from the plurality of other subjects.

2. The method of claim 1, further comprising adding a pre-defined value to each candidate R score if the subject is unable to complete the assessment task.

3. The method of claim 1, further comprising filtering the 3D kinematic data to remove noise by applying a 5 Hz, fourth-order Butterworth low-pass filter.

4. The method of claim 1, wherein collecting the 3D kinematic data from the kinematic sensor comprises receiving the 3D kinematic data wirelessly from the kinematic sensor over a wireless communication link.

5. The method of claim 1, wherein each respective candidate polynomial equation for oBESS is as follows: $oBESS = c1R^3 + c2R^2 + c3R^3 + c4$.

6. The method of claim 1, wherein the T is set at 20 seconds for the plurality of combinations of other candidate thresholds and other candidate durations.

7. The method of claim 1, wherein the windows are non-overlapping.

8. The method of claim 7, wherein the Tn is set at 5 seconds for the plurality of combinations of other candidate thresholds and other candidate durations.

* * * * *